United States Patent [19]

Chin

[11] Patent Number: 5,695,514
[45] Date of Patent: Dec. 9, 1997

[54] METHOD AND APPARATUS FOR HARVESTING BLOOD VESSELS

[75] Inventor: Albert K. Chin, Palo Alto, Calif.

[73] Assignee: Guidant Corporation, Indianapolis, Ind.

[21] Appl. No.: 616,425

[22] Filed: Mar. 15, 1996

Related U.S. Application Data

[63] Continuation-in-part of Ser. No. 593,533, Jan. 24, 1996, which is a continuation-in-part of Ser. No. 502,494, Jul. 13, 1995.

[51] Int. Cl.⁶ .................................................. A61B 17/00
[52] U.S. Cl. .......................... 606/190; 606/192; 606/159
[58] Field of Search ................................ 606/190, 192, 606/159; 129/898

[56] References Cited

U.S. PATENT DOCUMENTS

| | | | |
|---|---|---|---|
| 5,593,418 | 1/1997 | Mollenauer | 606/192 |
| 5,601,589 | 2/1997 | Fogarty et al. | 606/192 |

*Primary Examiner*—Michael Buiz
*Assistant Examiner*—Daphna Shai
*Attorney, Agent, or Firm*—Albert C. Smith; Fenwick & West LLP

[57] ABSTRACT

Apparatus and method of harvesting a vessel of interest use a thin-walled, dark-colored sheath inserted within the vessel with the aid of an inner, slidable support member that is removed following placement of the sheath within the length of the vessel of interest.

4 Claims, 3 Drawing Sheets

METHOD AND APPARATUS FOR HARVESTING BLOOD VESSELS

RELATED APPLICATIONS

This application is a continuation-in-part application of pending application Ser. No. 08/593,533, entitled "Tissue Dissection Cannula with Dissection Probe and Method", filed on Jan. 24, 1996 by Albert K. Chin, and still pending which is a continuation-in-part application of pending application Ser. No. 08/502,494, entitled "Tissue Separation Cannula and Method", filed on Jul. 13, 1995, by Albert K. Chin and still pending.

FIELD OF THE INVENTION

This invention relates to harvesting blood vessels, and more particularly to the method and apparatus for visually distinguishing a blood vessel from surrounding tissue.

BACKGROUND OF THE INVENTION

Selective advancement of a tapered tip balloon dissection cannula along a vessel to be harvested in order to form a working cavity adjacent the vessel commonly requires practice with an associated learning curve to distinguish the vein from surrounding tissue. Specifically, as the tapered tip of the dissection cannula is advanced along a vessel, the vessel is compressed in the region of contact with the tapered tip and the vessel attains a whitish appearance as visualized through the tapered tip, thus causing difficulty associated with visually distinguishing the compressed vessel from surrounding fat and connective tissue.

In addition, vessels that branch from the vessel to be harvested, for example, the saphenous vein may form a bifid system of divided vessels. One such divided and branched vessel may be incrementally larger and traverse a straighter course than the other divided or branched vessel, but visualization through the taper tip of the dissection cannula inhibits clear visual distinction between the branched vessels.

SUMMARY OF THE INVENTION

Apparatus and method in accordance with the present invention promotes visual distinction of the vessel to be harvested over surrounding tissue and branched vessels, and promotes lower probability of injury to the endothelium of the vessel as the dissection cannula is advanced outside the adventitia of the vessel in preparation for its harvest. Specifically, a dark or visually-contrasting thin-walled, hollow sheath with an internal support member is threaded through the vessel of interest odor to passage therealong of the dissection cannula. The support member is removed from the hollow sheath that remains in the vessel of interest to enhance its visual contrast against surrounding tissue as visualized through the transparent tapered tip of a balloon dissection cannula that is selectively advanced to form a working cavity in dissected tissue planes along the course of the vessel.

DETAILED DESCRIPTION OF THE PREFERRED EMBODIMENT

The apparatus and method of the present invention enhances the visual contrast of the vessel being 'harvested'. Specifically, as the cannula is advanced along a vein or artery, the blood inside the vessel is compressed out of the area in contact with the tapered tip, and the vessel attains a whitish appearance which is not easily distinguishable from the surrounding fat and connective tissue. With practice, the surgeon is able to visually distinguish the vessel from the surrounding tissue when viewed through the transparent tapered tip of a dissection cannula. Also, harvesting blood vessels requires special attention to the presence of branching vessels. For example, the saphenous vein may involve a bifid system in which the vein may divide into two branches that course along the leg. One desirable branch may be somewhat larger in diameter and run along a straighter course than the other less desirable branch. However, the larger, straighter branch may be hard to distinguish: visually through the transparent tapered tip of the dissection cannula.

Figure 1:
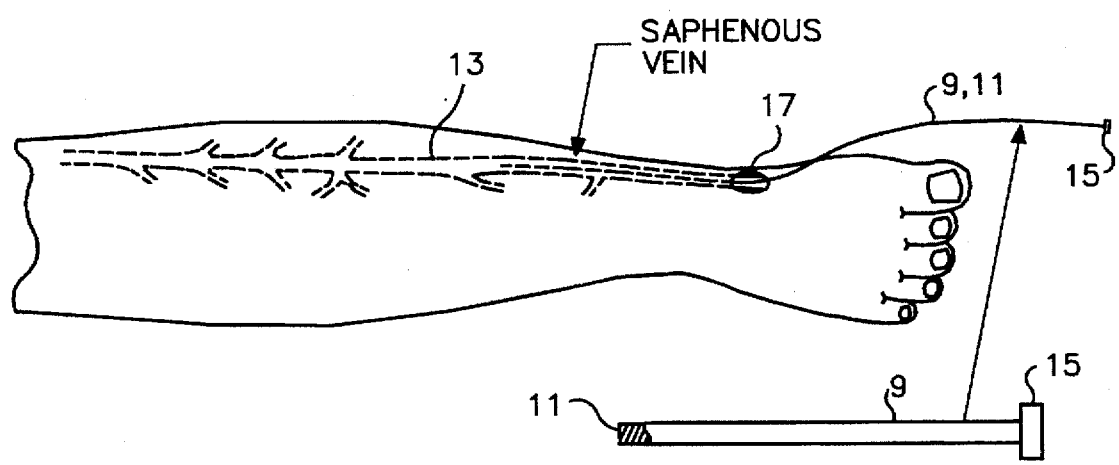
FIG. 1 is a partial pictorial illustration of the saphenous vein along a patient's leg with the combined structure of sheath and support member partially inserted in the vein.
Figure 2:
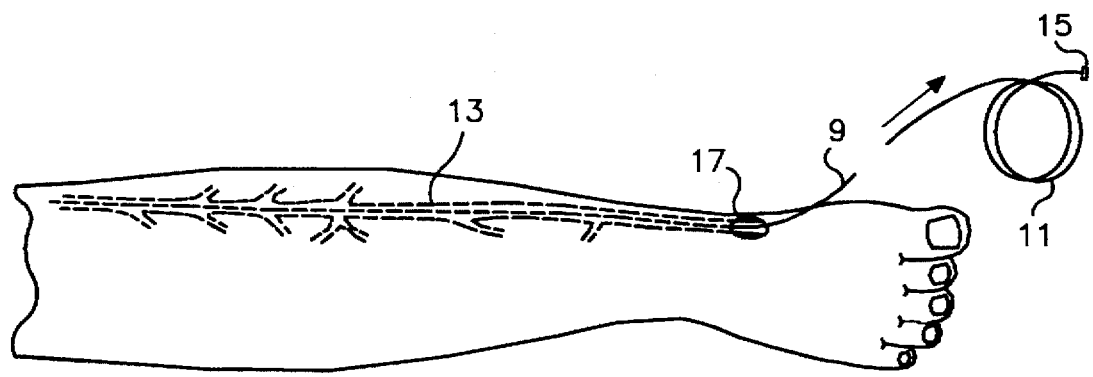
FIG. 2 is the pictorial illustration of the saphenous vein as in FIG. 1 with the hollow sheath in place and the support member removed.
Figure 3:
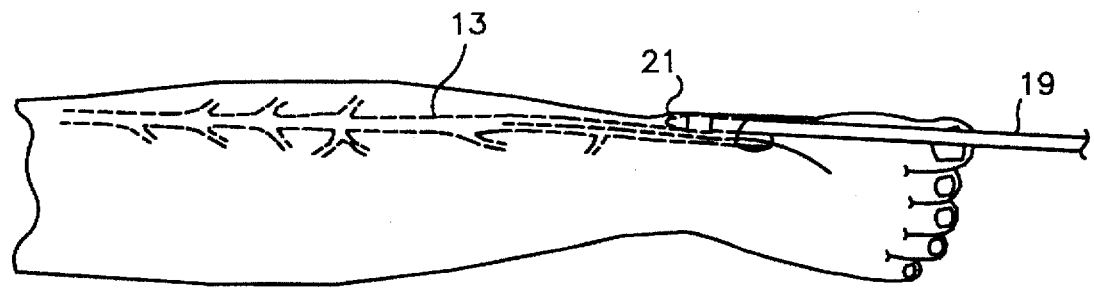
FIG. 3 is a partial pictorial illustration of the saphenous vein as in FIG. 1 with a dissection cannula partially advanced along the course of the vein.

Accordingly, as shown in FIG. 1, a thin-walled, dark colored, or contrastingly-.colored, sheath 9 with an internal support member 11 is initially threaded through the vessel of interest 13 prior to passage of a dissection 11 cannula along the length of the vessel to be harvested. The sheath 9 may be a tube with walls about 2 mil thick formed of Teflon or polyethylene or polyvinyl chloride or other bioinert material with a spring-like guidewire, a wire stylet, or a plastic catheter 11 as the support member slidably positioned inside the sheath 9. A knob 15 may be attached to the proximal end of the internal support member 11 to reference the hollow sheath 9 against an end of the structure, and to facilitate advancing the sheath 9 and support member 11 as a unit within the vessel of interest. The inner support member 11 provides column strength to allow the combined sheath 9 and support member 11 to be advanced the length of the vessel to be harvested from an incision 17 near one end thereof. For example, in harvesting a saphenous vein 13, an incision 17 is made at the ankle, and the saphenous vein 13 is isolated, and a small venotomy is performed to allow the combined structure of sheath 9 and inner support member 11 to be advanced along the length of the vein, through the leg and thigh to the groin. Following passage and placement of the sheath 9 and support member 11, the support member 11 is removed, as shown in FIG. 2, leaving the thin, flexible sheath 9 in place in the vein 13. As illustrated in FIG. 3, the dissection cannula 19 is inserted in the incision 17 and advanced along the vein 13 in the manner as described in the Related Applications cited above. Briefly, while visualizing the vein 13 through the transparent tapered tip 21 of the balloon dissection cannula 19, the vein 13 and internally-placed sheath 9 of visually contrasting color are readily distinguishable from surrounding fat and connective tissue. The peripheral balloon 23 is selectively inflated and deflated as the tip is advanced to form a working cavity into dissected tissue planes along the length of the vein to be harvested. As the cannula 19 advances, the dark color of the sheath 9 is visible through the vein 13, and cannula advancement is facilitated by the enhanced visibility of the vein 13 as shown in FIG. 3.

Figure 4:
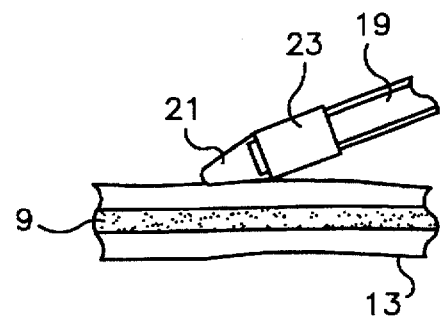
FIG. 4 is a pictorial, sectional view of the sheath within a segment of the saphenous vein adjacent the tip of the dissection cannula.
Figure 5:
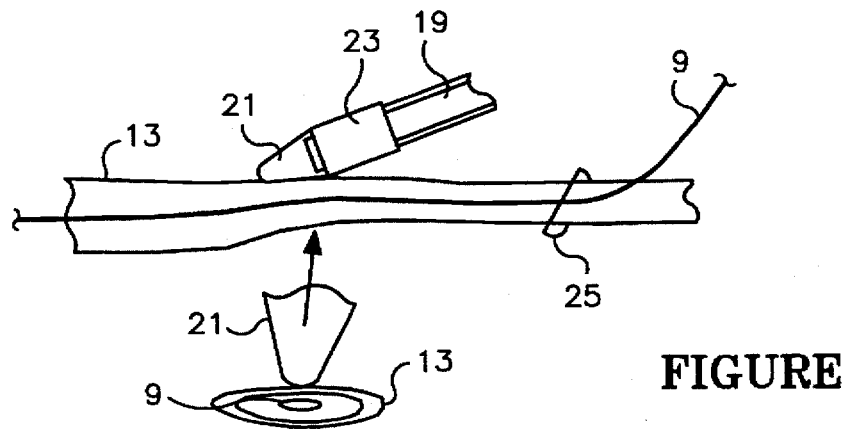
FIG. 5 is a simplified pictorial illustration of the physical interaction between the dissection cannula and the saphenous vein and the installed hollow sheath.

The thin sheath 9 does not injure the endothelium (inner lining) of the vein 13 as the cannula 19 is advanced along the adventitia (outer lining) of the vein 13, as shown in FIG. 4. If the tuner support member 11 was left in place, or if a dark colored catheter was used to cannulate the vein prior to passage of the dissection cannula, the squeezing or compressive force exerted on the vein by a cannula on the outside and an incompressible device on the inside may cause injury to the endothelium of the vessel, thereby shortening its life as a vascular graft. In addition, insertion of the combined sheath 9 and inner support member 11 tends to proceed along the straighter section of a bifid venous system. The visually-contrasting color of the sheath (e.g., black, green) 9 thus facilitates visually guiding the dissection cannula 19 via visualization through the transparent tapered tip 21 along the preferred branch of the bifid vein in which the sheath 9 is previously placed.

In an alternative embodiment, a single thin flexible guidewire may be used to cannulate the vessel in lieu of the sheath 9 and inner support member 11. However, the sheath and inner support member is preferable because it allows a larger-diameter, thin-walled sheath 9 to be placed, and the thin-walled sheath 9 forms a broad, dark stripe inside of the vessel that is better visualized through the transparent tapered tip of a dissection cannula than a thin, dark guidewire. Also, the thin-walled sheath 9 provides a broader-area, compressible member that cushions the walls of the vein 9 against squeezing or creasing injury attributable to contact of the vein 9 with the advancing cannula 19. Optionally, a hemostatic clip or clamp 25 may be positioned to occlude the vessel 13 and sheath 9 to control bleeding during the vessel harvesting procedure.

Figure 6:
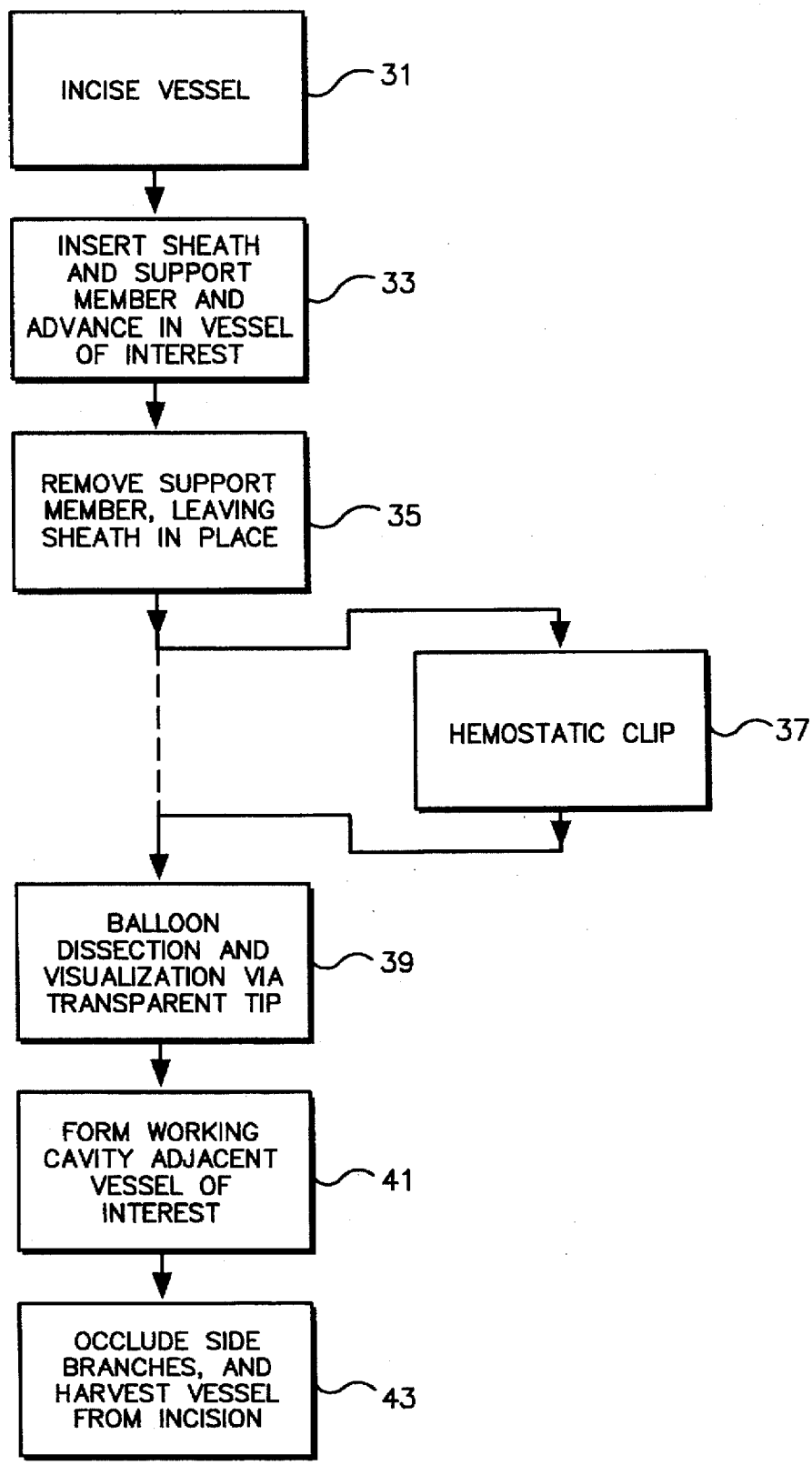
FIG. 6 is a flow chart illustrating the procedure according to the present invention.

Referring now to the flow chart of FIG. 6, there is shown a graphic illustration of the method according to the present invention. An incision 31 is made to expose the vessel of interest (e.g., the saphenous vein) and a combined structure of a thin-walled, dark or contrastingly colored sheath with an internal support member slidably disposed therein is inserted 33 into the vein of interest through a small venotomy and is pushed and otherwise advanced along the length thereof from the incision. The inner support member is removed 35 from the sheath, leaving the sheath in place within the length of the vessel of interest. Optionally, a hemostatic clip may be installed 37 about the vessel and sheath to control bleeding during the vessel-harvesting procedures.

A tapered-tip, balloon dissection cannula is next inserted 39 in He incision adjacent the vessel of interest, and is selectively advanced along the vessel while visualizing through the transparent tapered tip the vessel of interest with the contrastingly colored inner sheath in place. A peripheral balloon of the dissection cannula may be selectively inflated and deflated as the tip is advanced to form a working cavity 41 within dissected tissue planes adjacent the vessel of interest. Side-branch vessels from the vessel of interest may be occluded 43 with clips or sutures and ligated from within the working cavity. The sheath 9 may then be removed and the resulting skeletonized vessel of interest may then be harvested between the incision and another incision at a spaced location along the length of the vessel of interest. Alternatively, the vessel of interest may be harvested with the sheath 9 in place to inhibit excessive stretching and other sources of injury to the vessel walls as the vessel is removed from within the working cavity through an incision at a location along the length of the vessel. Of course, a sheath of contrasting visual characteristics may also be inserted within an artery of interest for harvesting in accordance with the present invention to enhance visual discrimination of the arterial vessel from surrounding tissue as a dissection cannula is advanced along such an artery to form a working cavity within dissected tissue planes adjacent the artery of interest.

Therefore, the method and apparatus of the present invention facilitates visual discrimination of the vessel of interest from surrounding fat and connective tissue, and reduces the possibility of injuring the endothelium of the vessel during preparation for harvesting.

I claim:

1. A method for harvesting a blood vessel of interest using a dissection cannula having a transparent tapered tip, the method comprising the steps of:

forming an incision to isolate the vessel of interest;

making an incision in the isolated vessel of interest;

inserting via the incision in the vessel of interest and along the length thereof a hollow sheath of bioinert material having a visually contrasting characteristic;

inserting the dissection cannula adjacent the vessel of interest with the transparent tapered tip thereof disposed to visualize the vessel of interest with the sheath of visually contrasting characteristic visible within the vessel of interest through the transparent tapered tip;

advancing the dissection cannula along the vessel of interest to form a working cavity within dissected tissue planes adjacent the vessel of interest;

occluding and ligating side branches of the vessel of interest within the working cavity; and harvesting the vessel of interest through the incision.

2. The method according to claim 1 wherein the step of inserting a hollow sheath includes inserting a support member therewith slidably disposed within the hollow sheath to provide sufficient rigidity to facilitate advancement of the combined structure of hollow sheath and support member therewithin along a selected length of the vessel of interest.

3. The method according to claim 2 including the additional step of:

slidably removing the support member from within the hollow sheath following placement of the combined structure along the selected length of the vessel of interest.

4. A method for harvesting a blood vessel of interest using a dissection cannula having a transparent tapered tip, the method comprising the steps of:

forming an incision to isolate the vessel of interest;

making a small incision in the isolated vessel;

inserting via the incision in the vessel and along the length of the vessel of interest a small diameter probe having a visually contrasting characteristic;

inserting the dissection cannula adjacent the vessel of interest with the transparent tapered tip thereof disposed to visualize the vessel of interest with the probe of visually contrasting characteristic visible within the vessel of interest through the transparent tapered tip;

advancing the dissection cannula along the vessel of interest to form a working cavity within dissected tissue planes adjacent the vessel of interest;

occluding and ligating side branches of the vessel of interest within the working cavity; and harvesting the vessel of interest through the incision.

* * * * *